United States Patent [19]
Weber

[11] Patent Number: 6,085,425
[45] Date of Patent: Jul. 11, 2000

[54] SURGICAL CUTTER

[75] Inventor: Helmut Weber, Emmingen, Germany

[73] Assignee: KMedic Inc., Northvale, N.J.

[21] Appl. No.: 08/677,306

[22] Filed: Jul. 9, 1996

[51] Int. Cl.[7] .................................................. B26B 17/02
[52] U.S. Cl. ............................................. 30/192; 30/193
[58] Field of Search ........................... 30/186, 191, 192, 30/193, 175, 252, 242

[56] References Cited

U.S. PATENT DOCUMENTS

| | | | |
|---|---|---|---|
| 444,541 | 1/1891 | Porter . | |
| 790,617 | 5/1905 | Carolus . | |
| 914,910 | 3/1909 | Alley . | |
| 928,335 | 7/1909 | Ryden | 30/186 |
| 1,145,082 | 7/1915 | Porter . | |
| 1,472,392 | 10/1923 | Harvey . | |
| 2,583,346 | 1/1952 | Sprunger | 30/193 |
| 3,315,669 | 4/1967 | Rhodes . | |
| 3,324,549 | 6/1967 | Sharp | 30/193 |
| 3,340,611 | 9/1967 | Lauck . | |
| 4,441,388 | 4/1984 | Manor | 30/191 |
| 4,910,870 | 3/1990 | Chang . | |
| 5,187,869 | 2/1993 | Heiss | 30/191 |
| 5,272,810 | 12/1993 | Orthey . | |

OTHER PUBLICATIONS

Orthopedic Instruments Guide, 1996, K–Medic, pp. Q13–Q19.

*Primary Examiner*—Hwei-Siu Payer
*Attorney, Agent, or Firm*—Hughes Hubbard & Reed LLP; Ronald Abramson; Peter A. Sullivan

[57] ABSTRACT

The present invention is directed toward a surgical cutter for wires, pins and rods, especially spinal rods, having two cooperating jaws pivotally secured in between two holding plates by floating bolts, and having said jaws pivotally secured to two handles by freely floating bolts, so that when the handles are pushed together the jaws close and cut an object placed therein, and when the handles are pulled apart the jaws open to permit placement of an object for cutting therebetween, wherein further the handles are precisely designed to form a non-adjustable stop limiting the opening of the jaws when the handles are pulled apart and preventing the jaws from closing beyond a predetermined point when the handles are pushed together.

14 Claims, 5 Drawing Sheets

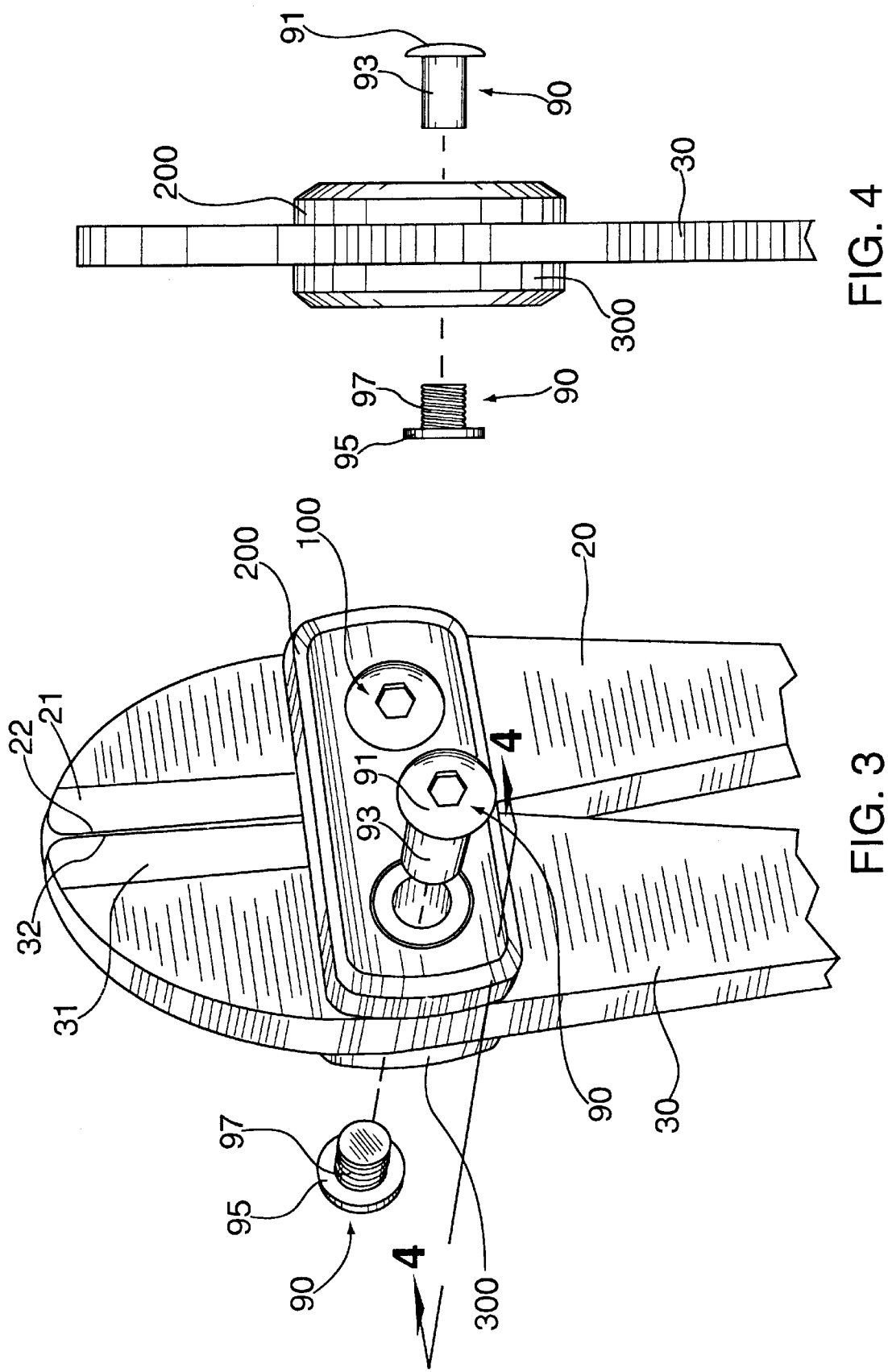

SURGICAL CUTTER

FILED OF THE INVENTION

The present invention relates generally to a surgical instrument, and more particularly to an improved surgical cutter for wires, pins and rods, especially spinal rods.

BACKGROUND OF THE INVENTION

Wires, pins and rods are implanted by orthopedic and other surgeons in patients to aid in the alignment, reduction, and fixation of fractured bones. Wires, pins and rods are available in several standard lengths and in a range of diameters. Since an application may require a wire, pin or rod of a length that may not be available from a manufacturer, surgical cutters are used by surgeons and others to cut wires, pins, or rods to the desired length.

In the past, surgeons relied on hardware store quality cutters for cutting wires, pins and rods. Although manufactures of surgical instruments have now developed cutters more suitable for operating room applications, cutters still suffer from a number of limitations which cause the early breakdown of the cutters, and particularly the breakdown of the jaws of the cutter.

It is known in the art that quality jaws should be manufactured using a tough specially-tempered tool steel such as 400 series stainless steel. Quality jaws are currently manufactured from a 400 series stainless steel that is cut in cross-sections from large steel bars. A jaw that is manufactured from stainless steel that is cut in cross-sections from large steel bars has a cross-grained structure, which cross-grained structure is not best adapted to the increasing hardness of spinal rods which are used today by surgeons and which, hence, need to be cut by the cutters. In accordance with one aspect of the present invention, the jaws of the cutter are improved in that they are manufactured using 400 series stainless steel bar stock that has been rolled to the width and thickness of jaws so that the stainless steel in the jaw has a linear-grained structure. A jaw made from linear-grained structure stainless steel has a harder and thus longer-lasting jaw cutting edge.

The cutting edges of the jaws of prior art cutters have been hand-ground, resulting in slight inconsistencies in the geometry of the jaw cutting edge. These slight inconsistencies in the geometry of the cutting edge contribute to the early breakage of the cutting edge due to stress. In accordance with another aspect of the present invention, the jaws and jaw cutting edges are improved in that they are manufactured using Computer Numerical Control technology. Computer Numerical Control technology manufactured jaws and cutting edges are precise. The jaws have the same symmetrical settings along the entire jaw cutting edges. Cutting edges with precise symmetrically-machined angles require less cutting force than un-even hand-sharpened cutting edges since the flow of material (material displacement) is symmetric. Moreover, the jaws and the jaw cutting edges last longer because they can better withstand the stress of cutting.

Manufactures of cutters have recognized the necessity of placing an adjustable stop on the handle of a cutter to correctly calibrate the timing of the jaw shut-off (where the jaws naturally come together and stop) and handle-stop (such as where the jaws are stopped by an immovable/unadjustable bar on a handle). Because of the inconsistencies of the jaw cutting edge, the imprecise construction, and slight variances due to threaded bolt design, an adjustable stop was necessary to correctly set the timing of jaw shut-off and the handle-stop action of the cutter. Such adjustable stops allow individuals to adjust the point where the jaws meet and the maximum force or pressure that can be applied to the jaw edges before hitting the handle stop. With incorrect adjustment by an untrained individual, however, the time between jaw shut-off and handle-stop can be lengthened resulting in more force being placed on the jaw edges than the cutter is intended to endure during the cutting process and this ultimately will cause jaw overload and jaw breakage. In accordance with another aspect of the present invention, the cutter is improved in that the handles are designed with a precise non-adjustable stop. This feature protects the cutter from jaw overload. That is, in the improved cutter, the handle-stop (jaw shut-off) has been designed without an adjustment option, and the handle stop and jaw closure are precisely adjusted to cut a particular diameter wire, pin and/or rod correctly. The resulting cutting consistency contributes to a longer life for the cutting edges of the jaws.

The jaws of prior art cutters, with use, become increasingly tight because many of such cutters consist of two jaws which are held between two holding plates by two threaded bolts. Over time, the threaded bolts cause the jaws to actually bind and perhaps to stop functioning altogether. This binding adds stress on the bolts, which stress can result in shearing of the bolts especially at thread diameter. Moreover, since the spacing of the two holding plates is controlled by the pitch of the threading on the bolts, the spacing between the holding plates is not completely uniform and precise, causing additional stress. In accordance with another aspect of the present invention, the improved cutter resolves these problems by the use of a free "floating" bolt. The floating bolt is not threaded to the jaws or to the holding plates and it allows the jaws to freely pivot about the bolt. The floating bolt consists of a cap-bolt which is threaded into an internally threaded bushing. When the cap-bolt is fully threaded into the bushing, it secures the jaws/holding plate assembly together but nothing mechanically connects it to the jaws/holding plate assembly, hence it is a floating bolt allowing the jaws to freely pivot. Similarly, the floating bolt secures the jaw/handle assembly together but nothing mechanically connects the floating bolt to the jaw/handle assembly. The free floating bolts connected to the jaws prevent stress build-up and tightening on the jaws. The free floating bolts connected to the jaws also prevent binding or clamping of the holding plates to the jaws. The precise spacing between the jaw/holding plate assembly also prevents stress build-up and tightening. Stress on the bolts themselves is lessened and therefore the bolts are not sheared during cutting.

Several prior patents describe cutters and their features including U.S. Pat. Nos. 5,272,810 to Orthey, 4,910,870 to Chang; 3,340,611 to Lauck; 3,315,669 to Rhodes; 1,472,392 to Harvey; 1,145,082 to Porter; 914,910 to Alley; 790,617 to Carolus; and 444,541 to Porter. None of these patents, however, employ the improved features and structural configuration of the cutter of the present invention.

OBJECTS OF THE INVENTION

An object of the present invention is to provide an improved cutter having a harder and thus longer-lasting jaw cutting edge.

Another object of the present invention is to provide an improved cutter having jaws and jaw cutting edges which are precise and have the same symmetrical settings along the entire jaw cutting edge, thus requiring less cutting force than un-even hand-sharpened cutting edges, and having jaws and jaw cutting edges which last longer because they can better withstand the stress of cutting.

Another object of the present invention is to provide an improved cutter having a non-adjustable stop to avoid jaw overload.

Another object of the present invention is to provide an improved cutter having a construction that avoids jaw binding or and/or binding or clamping of the holding plates to the jaws.

Another object of the present invention is to provide an improved cutter having a construction which prevents stress or stress build-up on the bolts used therein, which stress can result in shearing of the bolts especially at thread diameter as a consequence of use of the cutter.

It is a further object of the present invention to improve upon the disadvantages of the prior art.

Still other advantages of the invention, and the invention itself, will become more apparent and may best be understood from the following description, which description is illustrated by the accompanying drawings, in which:

BRIEF DESCRIPTION OF THE DRAWINGS

FIG. 3 is a partially exploded perspective view of a portion of the cutter shown in FIG. 1 showing the jaws and holding plates of the cutter, wherein the jaws are shown in a closed position and the holding plates are shown in position on the front side and the back side of the jaws, and one of the free floating bolts is exploded.

FIG. 4 is a partially exploded side view of the cutter shown in FIG. 1 showing the jaws and holding plates of the cutter, wherein one of the two free floating bolts of the jaw/holding plate assembly is exploded.

SUMMARY OF THE INVENTION

The improved surgical cutter for cutting wires, pins and rods, especially spinal rods, of the invention has two cooperating jaws pivotally secured by a first securing means in between two holding plates, and has the first of said jaw pivotally secured by a second securing means to a first handle and the second of said jaw pivotally secured by said second securing means to a second handle, so that when said handles are pushed (compressed or squeezed) together the said jaws close to cut an object placed therein, and when said handles are pulled apart said jaws open to permit placement of an object for cutting therebetween, wherein the improvement resides in that at least one of said first or second securing means comprises at least one floating bolt. In a preferred embodiment, the jaws are manufactured from a linear-grained stainless-steel, the jaws are manufactured using Computer Numerical Control Technology, and the floating bolts, which comprise a cap-bolt and an internally threaded bushing, are placed in the cutter in a predetermined manner.

DETAILED DESCRIPTION OF THE PREFERRED EMBODIMENTS

Figure 1:
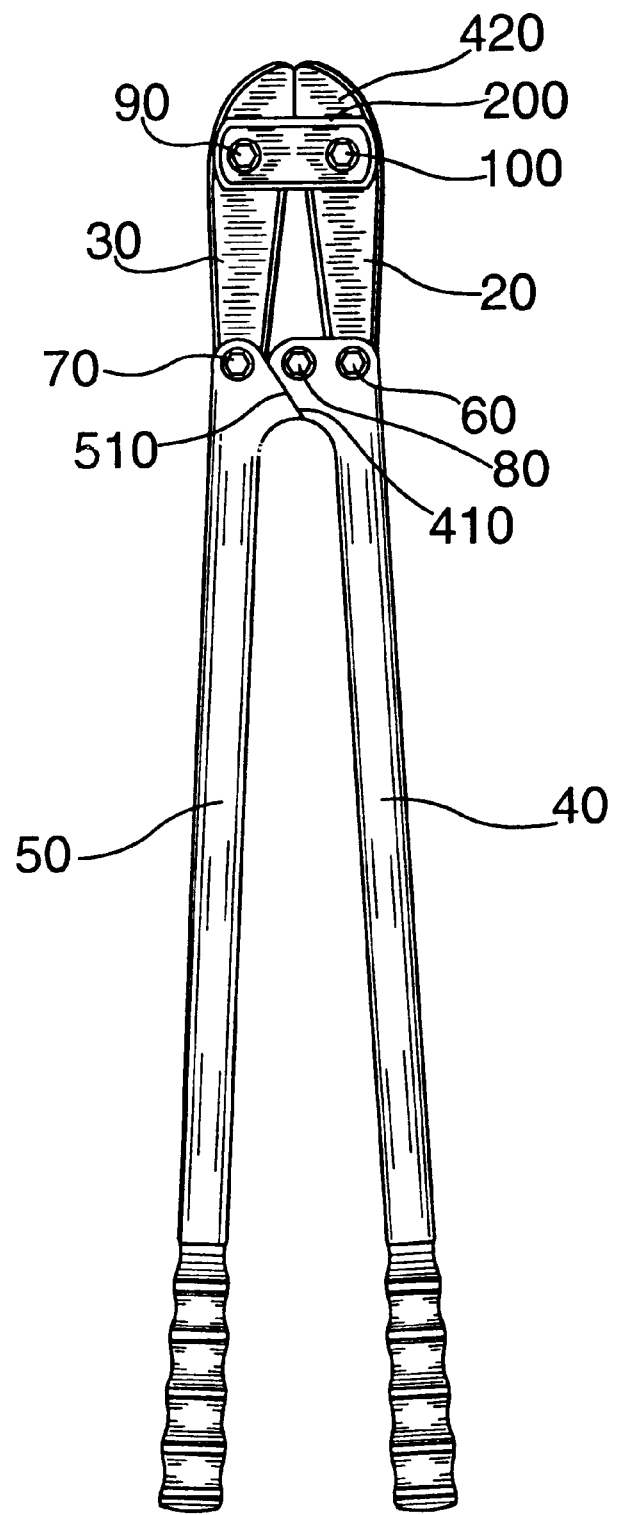
FIG. 1 is a front view of the cutter of the invention, where the jaws thereof are shown in the closed position when the handles are in closed position.

Referring to FIGS. 1 through 6, a preferred embodiment of the cutter is shown in FIG. 1 wherein said cutter includes handles 40 and 50 and a pair of cooperating jaws 20, 30. Jaw 20 has cutting edge 21 and jaw 30 has cutting edge 31 (see FIG. 3).

Figure 5:
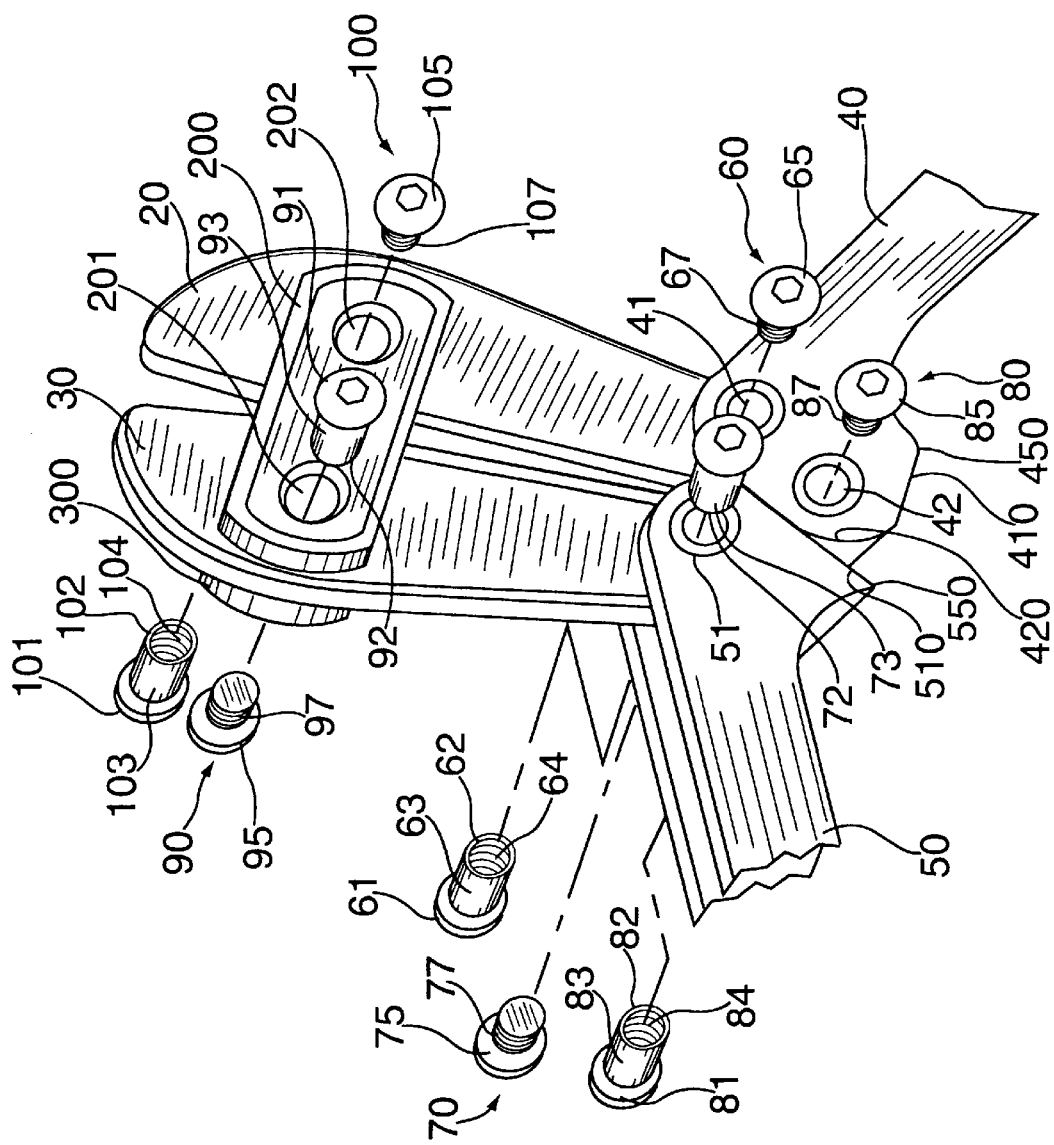
FIG. 5 is a partially exploded perspective view of the jaws, the holding plates, and the upper portion of the handles of the cutter shown in FIG. 2, wherein the preferred orientation of the five free floating bolts is shown.
Figure 6:
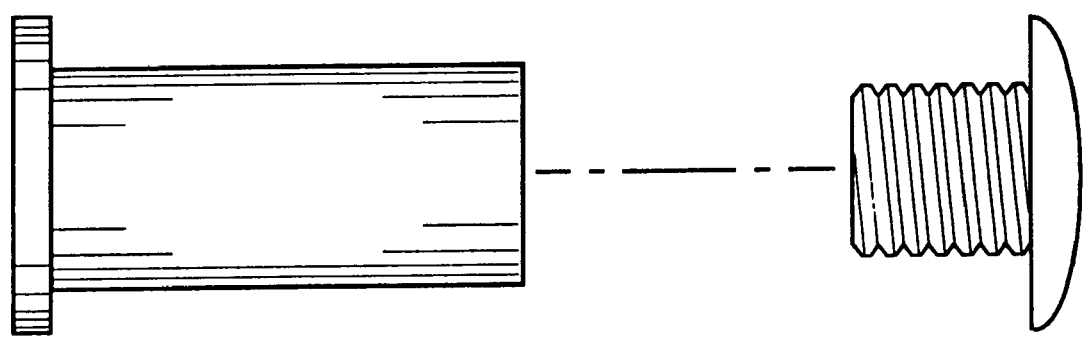
FIG. 6 is a side view of the floating bolt, exploded to show the cap-bolt on the right side of the figure and the bushing on the left side of the figure.

The jaws are pivotally connected to the handles by floating bolts. Specifically, jaw 20 is pivotally connected to handle 40 by floating bolt 60 and jaw 30 is pivotally connected to handle 50 by floating bolt 70. A pair of holding plates 200, 300 are disposed on opposite sides of jaws 20 and 30. The jaws are pivotally connected to holding plates 200, 300 by floating bolts. Specifically, jaw 20 is pivotally connected to holding plates 200, 300 by floating bolt 100 and jaw 30 is pivotally connected to holding plate 200, 300 by floating bolt 90. As best seen in FIG. 5, floating bolt 100 passes through hole 202 in holding plate 200, a corresponding hole in jaw 20 and a corresponding hole in holding plate 300. Floating bolt 100 is not threaded or engaged into holding plate 200, jaw 20 or holding plate 300. Floating bolt 90 passes through hole 201 in holding plate 200, a corresponding hole in jaw 30 and a corresponding hole in holding plate 300. Floating bolt 90 is not threaded or engaged into holding plate 200, jaw 30 or holding plate 300. The floating bolts are designed to provide a fit which will not loosen during use and will not result in clamping or tightening. They have a precise, unchanging dimension that is slightly larger than the thickness of the jaws and holding plates.

To further prevent clamping or tightening of the jaws during use, the floating bolts are arranged in the preferred cutter in the specific orientation shown in FIG. 5. Floating bolt 90 comprises a cap-bolt 95 and an internally threaded bushing 91. In the embodiment shown, bushing 91 is inserted into hole 201 of holding plate 200, then into a corresponding hole in jaw 30 and finally into a corresponding hole in holding plate 300. Cap-bolt 95 is inserted first into a hole in holding plate 300, then into a corresponding hole in jaw 30, etc. The threading 97 on cap-bolt 95 is threaded into the internal threading of bushing 91. Shaft 93 of bushing 91 is smooth. When fully threaded, the end 92 of shaft 93 of bushing 91 is engaged against the inner side of cap-bolt 95 which is closest to the threaded portion 97 of cap-bolt 95.

Floating bolt 100 also comprises a cap-bolt 105 and an internally threaded bushing 101. In the embodiment shown, bushing 101 is inserted into a hole in holding plate 300, then through a corresponding hole in jaw 20, and then through hole 202 of holding plate 200. The cap-bolt 105 is inserted first into hole 202 of holding plate 200. The threading 107 on cap-bolt 105 is threaded into the internal threading 104 of bushing 101. Shaft 103 of bushing 101 is smooth. When fully threaded, the end 102 of the shaft 103 of bushing 101 is engaged against the inner side of cap-bolt 105 which is closest to the threaded portion 107 of cap-bolt 105. Thus, the floating bolts in each of the jaws are oriented in opposite directions. Referring to FIG. 5, cap-bolt 105 is inserted into bushing 101 by holding the bushing with one alien wrench and by turning the cap-bolt with another allen wrench in a clockwise direction. Bushing 91 is inserted into cap-bolt 95 by turning the hexagon pocket of the bushing or of the cap-bolt the same way.

During use of the cutter, bushing ends 62, 72, 82, 92, 102 of hollow female portions 63, 73, 83, 93 and 103 of each bushing 61, 71, 81, 91, 101 respectively act as a stop to tightening of the cap-bolt into the bushing so that tightening of the jaws does not occur as it would with a conventional bolt and nut.

All of the stress generated during the cutting process rests on the large uniform diameter free floating bolts 60, 70, 80, 90 and 100 having respective threaded male members 67, 77, 87, 97 and 107 respectively insertable within corresponding hollow female portions 63, 73, 83, 93 and 103 of respective bushings 61, 71, 81, 91 and 101. The free floating bolts are not adversely effected by the stress and will not bind as a result of repeated use.

Also, since the floating bolts are of a uniform length, the holding plates/jaw assembly operates smoothly and precisely compared to prior art cutters having bolts that are threaded and tightened by a nut. Such prior art bolts, because of the pitch of the threading of the bolt, have uneven spacing between the jaws and holding plates. Spacing which is not uniform or precise causes stress during cutting.

The bushings used are made out of heat-treated stainless steel so that they can better withstand the stress of use. In the preferred embodiment, the cap-bolt and bushing are joined, threaded and tightened to each other in a precise, unchanging dimension that is slightly larger than the thickness of the jaws and holding plates. The bolts are thus essentially flush-mounted on the jaw/holding plate assembly and on the jaw/handle assembly. The free-floating design creates enough play to eliminate the chance of binding, but still is precise enough to ensure cutting accuracy.

The free floating bolts are flush mounted. This flush mounting reduces the width of the jaw/holding plate assembly and eliminates any sharp edges. There are no sharp edges to get caught in clothing and the flush mounting also makes it difficult for bolts to be accidently loosened.

Handle 40 is pivotally connected to jaw 20 by floating bolt 60. Handle 50 is pivotally connected to jaw 30 by floating bolt 70. In the preferred embodiment, cap-bolt 65 of floating bolt 60 with threading 67 is placed into hole 41 in handle 40 and bushing 61 with internal threading 64 is placed in the corresponding hole in handle 40 from the other (back) direction (see FIG. 5) so that bushing 61 engages cap-bolt 65 and cap-bolt 65 can be threaded into bushing 61. Also, cap-bolt 85 of floating bolt 80 with threading 87 is placed into hole 42 and bushing 81 with internal threading 84 is placed in the corresponding hole from the other direction so that it engages cap-bolt 85 and cap-bolt 85 can be threaded into bushing 81. Thus, in the preferred embodiment, it can be seen that the floating bolts in handle 40 and the floating bolt in jaw 20 are placed in the same manner through the holes, i.e., cap-bolts are inserted into their respective holes from the front of the cutter and the bushings are inserted into their respective holes from the back of the cutter.

Also, bushing 71 of floating bolt 70 is placed into hole 51 in handle 50 and cap-bolt 75 of floating bolt 70 is placed in the corresponding hole from the other direction so that it meets with bushing 71 and cap-bolt 75 can be threaded into bushing 71. Thus, in the preferred embodiment, it can be seen that the floating bolt in handle 50 and the floating bolt in jaw 30 are placed in the same manner through the holes, i.e., cap-bolts are inserted into their respective holes from the back of the cutter and the bushings are inserted into their respective holes from the front of the cutter.

During use, the free floating bolt construction and opposing bolt placement/orientation prevent the cap-bolt from becoming loose. Bolts generally become loose because of axial pressure combined with radial movement and friction caused during use. During the cutting process, pressure is applied to the jaw edges. A very small amount of this force is diverted sideways to the holding plates and to the shoulders of the free floating bolts. This sideways pressure combined with pivoting action and friction between the holding plates and the shoulders of the bolts can tend to turn and loosen the cap-bolt. Cap-bolts are thus placed on the sides where the friction and pivoting action will tend to tighten the cap-bolt rather than loosen it. In the cutter, the cap-bolts are positioned on the front side of right hand assembly (65, 85, 105) in FIG. 5 and cap-bolts are positioned on the back side of the left hand assembly (75, 95). This right and left side placement is necessary to prevent the cap-bolts from becoming loose. In the preferred embodiment, thread cement is also used in the free floating bolts. This is because cutters are cleaned in an ultrasonic cleaner and sterilized in an autoclave. The ultrasonic cleaner causes vibration and sterilization causes expansion and contraction. This process of cleaning and autoclaving can cause a cap-bolt and bushing to become loose. To ensure that this does not happen, the threaded portion of the cap-bolt and bushing is cemented with a compound that withstands both ultrasonic cleaning and autoclaving.

Figure 2:
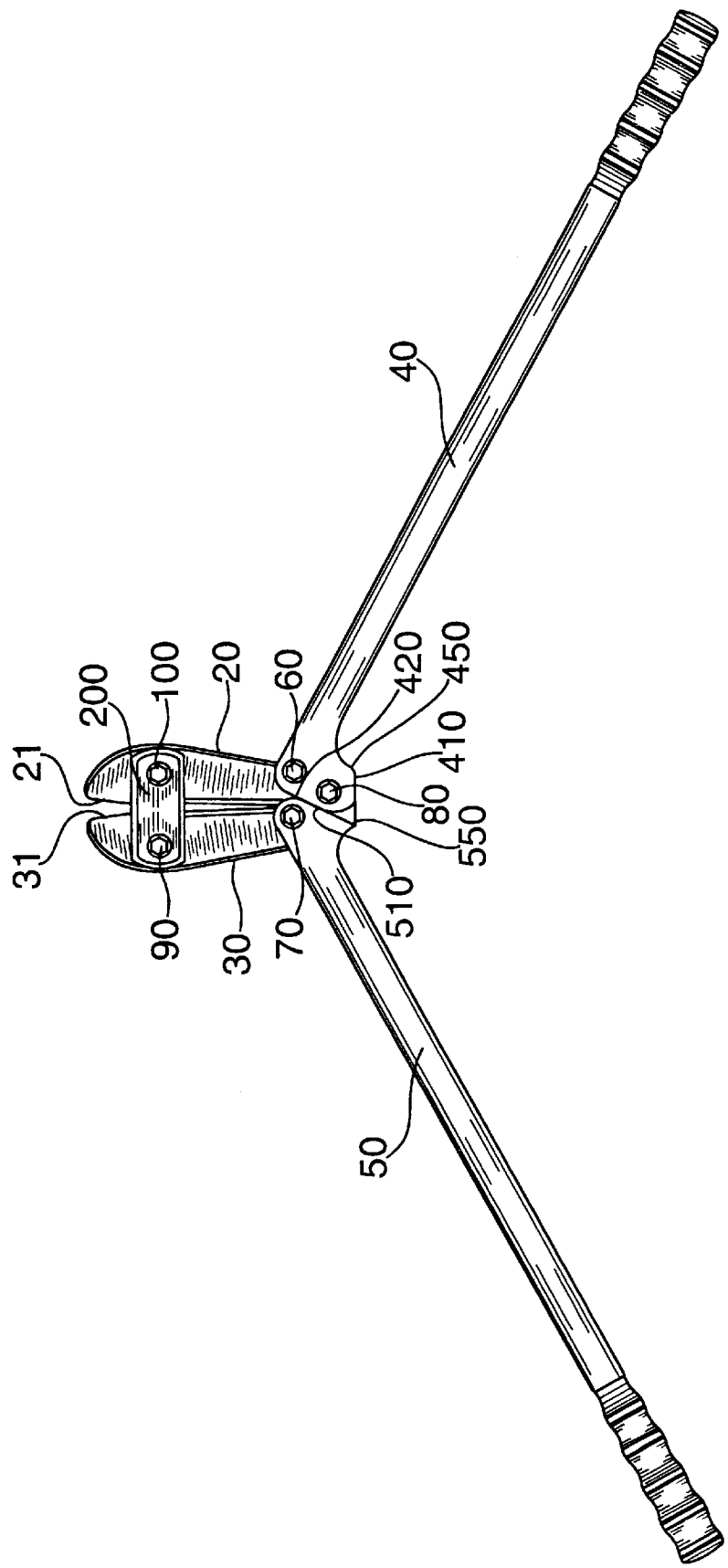
FIG. 2 is a front view of the cutter shown in FIG. 1, showing the jaws of the cutter in an open position (when the handles are in an open position) so that a wire, pin or rod of the requisite diameter can be inserted between the jaws of the cutter for cutting said wire, pin or rod.

When the cutter is in an assembled relationship as shown in FIG. 1 and the handles are closed, the jaws 20, 30 are closed. When jaws 20 and 30 are closed, surface 410 of handle 40 is in contact with surface 510 of handle 50 at respective ends of respective handles 40, 50. When the handles are opened as shown in FIG. 2, the jaws will be caused to pivot to an open position with the cutting edges 21, 31 of distal end portions of 22, 32 of jaws 20, 30 spread. As seen in FIG. 2, the stop surface 510 on handle 50 will engage the stop surface 420 on handle 40 to limit jaw opening. The cutting consistency gained by having a precision handle-stop (jaw shut-off) contribute to longer cutting edge life. These surfaces are precisely manufactured to serve as a stop and they are designed so as not to be adjustable. When a wire, pin or rod to be cut is inserted between the jaws, and the handles are pushed together, the jaws pivot to the closed position about floating bolts 90 and 100. The handles and jaws also pivot with respect to each other about floating bolts 60 and 70. When the handles are pushed together, floating bolts 60 and 70 move away from each other, and floating bolt 80 moves between floating bolts 70 and 60. Handle part 450 of handle 40 and handle part 550 of handle 50 are joined together with tongue and groove. When the handles are pulled apart, floating bolts 60 and 70 move toward each other and handle part 450 and handle part 550 move apart.

As can be seen in FIG. 3, the floating bolts are readily removable by use of two appropriately sized allen wrenches and are hence easily replaceable. In the event that a jaw breaks, or is worn, it too can be readily removed and replaced by removal of the appropriate floating bolts.

As previously noted, the jaws are manufactured using 400 series stainless steel bar stock that has been rolled to the width and thickness of the jaw. This assures linear-grained structure in the stainless steel which maximizes the strength of the stainless steel. The linear grained structure produces a harder, longer-lasting jaw edge. 400 series stainless steel with linear-grained structure fully heat-treated and annealing with 280° F. (autoclave temperature) can gain 1 to 2 Rockwell hardness verses 400 series stainless steel with a cross-grained structure.

Also, the jaws of the cutter are manufactured using CNC (Computer Numeral Control). Such jaws and cutting edges are precise and have the same symmetrical settings along the jaw edge.

Cutting edges with precise symmetrically-machined angles will need less cutting force than cutters having uneven hand-sharpened cutting edges. In CNC manufactured jaws, the flow of material (material displacement) is symmetric, and therefore less cutting force needs to be exerted to perform a given cutting task.

It is noted that modifications may be made to the preferred embodiment of the present invention without departing from the spirit and scope of the invention.

I claim:

1. An improved surgical cutter for cutting wires, sins and rods having two cooperating jaws pivotally secured by a first securing means in between two holding plates, and having the first of said jaws pivotally secured by a second securing means to a first handle and the second of said jaws pivotally secured by said second securing means to a second handle, so that when said handles are pushed together the said jaws close to cut an object placed therein, and when said handles are pulled apart said jaws open to permit placement of an object for cutting therebetween, wherein the improvement resides in that said first securing means comprises two floating bolts and said second securing means comprises two floating bolts, wherein floating bolts on a right side of said cutter are oriented so that cap-bolts are mounted from the front of the cutter to engage corresponding bushings mounted from the back of the cutter, and floating bolts on the left side of the cutter are oriented so that cap-bolts are mounted from the back of the cutter to engage corresponding bushings mounted from the front of the cutter.

2. The improved surgical cutter of claim 1 wherein said two floating bolts of said first securing means and said two floating bolts of said second securing means are formed of stainless steel.

3. The improved surgical cutter of claim 1 wherein at least one jaw of said jaws is formed of 400 series stainless steel bar stock that has been rolled to the width and thickness of said jaw so that said stainless steel in said jaw has a linear-grained structure.

4. The improved surgical cutter of claim 1 wherein at least one jaw is manufactured using Computer Numeral Control technology so that said at least one jaw and the cutting edge of said at least one jaw have the same symmetrical settings along said cutting edge.

5. An improved surgical cutter for cutting wires, pins and rods having two cooperating jaws pivotally secured by a first securing means, and having the first of said jaws pivotally secured by a second securing means to a first handle and the second of said jaws pivotally secured by said second securing means to a second handle, so that when said handles are pushed together the said jaws close to cut an object placed therein, and when said handles are pulled apart said jaws open to permit placement of an object for cutting therebetween, wherein the improvement resides in that at least one of said first or second securing means comprises at least one floating bolt and wherein when said handles are pulled apart, an upper surface of said second handle faces a side surface of said first handle to form a stop preventing said jaws from opening beyond a predetermined amount, and when the handles are pushed together, a side surface of said second handle faces the said side surface of said first handle to form a stop preventing said jaws from closing beyond a predetermined amount.

6. The improved surgical cutter of claim 5 wherein said at least one floating bolt is formed of stainless steel.

7. The improved surgical cutter of claim 5 wherein said at least one floating bolt comprises an internally threaded bushing and a cap-bolt which is adapted to be threadably engaged in said bushing.

8. The improved surgical cutter of claim 5 wherein at least one jaw of said jaws is formed of 400 series stainless steel bar stock that has been rolled to the width and thickness of said jaw so that said stainless steel in said jaw has a linear-grained structure.

9. The improved surgical cutter of claim 5 wherein at least one jaw of said jaws is manufactured using Computer Numerical Control technology so that said at least one jaw of said jaws and a cutting edge of said at least one jaw of said jaws have the same symmetrical settings along said cutting edge.

10. An improved surgical cutter for cutting wires, pins and rods having two cooperating jaws pivotally secured by a first securing means and having the first of said jaws pivotally secured by a second securing means to a first handle and the second of said jaws pivotally secured by said second securing means to a second handle, so that when said handles are pushed together the said jaws close to cut an object placed therein, and when said handles are pulled apart said jaws open to permit placement of an object for cutting therebetween, wherein the improvement resides in that said first securing means comprises at least one floating bolt and said second securing means comprises at least one floating bolt wherein when said handles are pulled apart, the upper surface of said second handle faces a side surface of said first handle to form a stop preventing said jaws from opening beyond a predetermined amount, and when the handles are pushed together, a side surface of said second handle faces the said side surface of said first handle to form a stop preventing said jaws from closing beyond a predetermined amount.

11. The improved surgical cutter of claim 10 wherein said at least one floating bolt of said first securing means and said at least one floating bolt of said second securing means are formed of stainless steel.

12. The improved surgical cutter of claim 10 wherein said at least one floating bolt of said first securing means and said at least one floating bolt of said second securing means comprise internally threaded bushings and cap-bolts which are to be threadably engaged in said bushings.

13. The improved surgical cutter of claim 10 wherein at least one jaw of said jaws is formed of 400 series stainless steel bar stock that has been rolled to the width and thickness of said jaw so that said stainless steel in said jaw has a linear-grained structure.

14. The improved surgical cutter of claim 10 wherein at least one jaw of said jaws is manufactured using Computer Numerical Control technology so that said at least one jaw of said jaws and a cutting edge of said at least one jaw of said jaws have the same symmetrical settings along said cutting edge.

* * * * *